(12) United States Patent
Hashman et al.

(10) Patent No.: US 8,119,567 B2
(45) Date of Patent: Feb. 21, 2012

(54) METHOD FOR CONTROL OF CYANOBACTERIAL ALGAE, MOSSES, LIVERWORTS, HORNWORTS AND OTHER BRYOPHYTES

(75) Inventors: Thomas E. Hashman, West Chester, PA (US); Kim Watson, Cherry Hill, NJ (US); John Long, Souderton, PA (US)

(73) Assignee: FMC Corporation, Philadelphia, PA (US)

( * ) Notice: Subject to any disclaimer, the term of this patent is extended or adjusted under 35 U.S.C. 154(b) by 1302 days.

(21) Appl. No.: 10/588,919

(22) PCT Filed: Feb. 9, 2005

(86) PCT No.: PCT/US2005/004352
§ 371 (c)(1),
(2), (4) Date: May 29, 2007

(87) PCT Pub. No.: WO2005/077172
PCT Pub. Date: Aug. 25, 2005

(65) Prior Publication Data
US 2007/0259788 A1    Nov. 8, 2007

Related U.S. Application Data

(60) Provisional application No. 60/543,794, filed on Feb. 11, 2004.

(51) Int. Cl.
*A01N 43/82* (2006.01)
(52) U.S. Cl. ........................................................ 504/262
(58) Field of Classification Search .................... None
See application file for complete search history.

(56) References Cited

U.S. PATENT DOCUMENTS 5,125,958 A    6/1992    Poss
6,703,349 B2   3/2004    Silverman et al.
6,710,017 B2 * 3/2004    Unhoch et al. ................ 504/150

FOREIGN PATENT DOCUMENTS

WO    WO 2004/106238 A2    12/2004

OTHER PUBLICATIONS

Koehler, Apple Spray Materials Cost per Dose, Associate Scientist—New England Pest Management Center/IPM/APHIS Revised Mar. 2001.*
Fourth Seminar of Algae Control Research Group, Feb. 24, 2003.*
Fausey (Controlling Liverwort and Moss now and in the future, HortTechnology, American Society for Horticultural Science, Jan.-Mar. 2008, 13(1) pp. 35-38.*
Peterson, et al., "Herbicide Mode of Action", Kansas State University, Jan. 2001. Pub. No. C715. Retrieved [online] at www.oznet.ksu.edu.
"Fourth Seminar of Algae Control Research Group" pamphlet from seminar by Japan Association for Advancement of Phyto-Regulators, on Feb. 24, 2003, Tokyo, Japan.
Fausey, J. C. "Controlling Liverwort and Moss Now and in the Future", HortTechnology, American Society for Horticultural Science, Jan.-Mar. 2003, 13(1) pp. 35-38.
Boger, P. et al. "Herbicide Classes in Development Mode of Action, Targets, Genetic Engineering, Chemistry," Springer 2002 pp. 254-259.

* cited by examiner

*Primary Examiner* — Alton Pryor

(57) ABSTRACT

Protoporphyrinogen oxidase enzyme-inhibiting herbicides are useful in a method for controlling unwanted cyanobacteria algae, mosses, liverworts, hornworts and other bryophytes. Of particular interest is the use of carfentrazone ethyl and certain metabolites thereof for control of unwanted cyanobacteria algae, mosses, liverworts, hornworts and other bryophytes.

8 Claims, No Drawings

METHOD FOR CONTROL OF CYANOBACTERIAL ALGAE, MOSSES, LIVERWORTS, HORNWORTS AND OTHER BRYOPHYTES

This application claims the benefit of U.S. Provisional Application No. 60/543,794, filed Feb. 11, 2004.

FIELD OF THE INVENTION

The present invention relates to the field of controlling unwanted cyanobacteria algae, mosses, liverworts, hornworts and other bryophytes.

BACKGROUND OF THE INVENTION

Cyanobacteria algae, mosses, liverworts, hornworts and other bryophytes are found growing in, on or adjacent to lawns, gardens, trees, shrubs, golf courses, rooftops, decks and concrete structures. They are non-parasitic, primitive green plants that have fine branched, threadlike stems with tiny leaves. The conditions that favor cyanobacteria algae, moss, liverwort, hornwort and other byrophyte growth include: excessive shade, high levels of moisture, acidic soil, compacted soil, low soil fertility or some combination of these conditions. Mosses typically form a thick, green mat on soil, roof, deck or concrete surfaces. Cyanobacteria algae can grow in similar ways. This growth impedes the surface's use or appearance and can also cause structural damage. Liverworts are similar in appearance to mosses and are often mistaken for moss. Physical removal, chemical treatment or combinations of both are generally used to achieve unwanted cyanobacteria algae, moss, liverwort, hornwort and other bryophyte control.

Physical removal is obviously time consuming, tedious and does not always result in the permanent removal of the unwanted cyanobacteria algae, mosses, liverworts, hornworts and other bryophytes.

Chemical treatment of unwanted cyanobacteria algae, mosses, liverworts, hornworts and other bryophytes requires the application of a chemical, i.e., a herbicide, to the area where the cyanobacteria algae, moss, liverwort, hornwort or other bryophyte is located. Herbicides known for use in control of these plants are heavy metal salts such as ferrous sulfate, ammonium sulfate, ferric ammonium sulfate and copper sulfate. There are considerable shortcomings in using the aforementioned herbicides. For example, these herbicides require very high use rates that can cause phytotoxicity to turf grasses and other plants in runoff conditions. High use rates also result in an accumulation of heavy metals in the soil and surrounding environment.

Clearly, chemical methods of treatment are lacking in some respects for the control of cyanobacteria algae, mosses, liverworts, hornworts and other byrophytes with the herbicides presently being used.

A newer class of herbicides different than those set forth above controls plants by disrupting certain functions in the plant cell. These herbicides are known as inhibitors of the enzyme protoporphyrinogen oxidase (commonly known as PPO-inhibitors), which cause disruption of cell membranes by inducing lipid peroxidation resulting in death to the plant. An example of an herbicidal PPO-inhibitor is carfentrazone-ethyl:

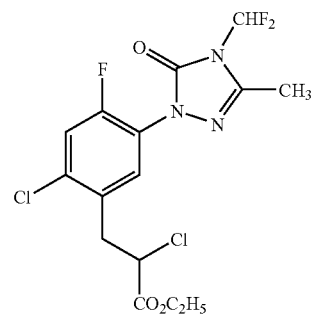

Carfentrazone-ethyl, namely ethyl α,2-dichloro-5-[4-(difluoromethyl)-4,5-dihydro-3-methyl-5-oxo-1H-1,2,4-triazol-1-yl]-4-fluorobenzenepropanoate, is disclosed and claimed in U.S. Pat. No. 5,125,958.

SUMMARY OF THE INVENTION

In accordance with the present invention, it has now been found that protoporphyrinogen oxidase enzyme-inhibiting (PPO-inhibiting) herbicides are useful in controlling unwanted cyanobacteria algae, mosses, liverworts, hornworts and other bryophytes at low use rates in, on or adjacent to lawns, gardens, trees, shrubs, golf courses, rooftops, decks and concrete structures. Specifically, the invention relates to a method for controlling unwanted cyanobacteria algae, mosses, liverworts, hornworts and other bryophytes, which comprises applying an effective amount of a protoporphyrinogen oxidase enzyme-inhibiting herbicide to a locus where said cyanobacteria algae, mosses, liverworts, hornworts and other bryophytes are growing or are expected to grow. Other aspects of the present invention will become apparent from the description below.

DETAILED DESCRIPTION OF THE INVENTION

One aspect of the present invention relates to a method for controlling unwanted cyanobacteria algae, mosses, liverworts, hornworts and other bryophytes, which comprises applying an effective amount of a protoporphyrinogen oxidase enzyme-inhibiting herbicide to a locus where said cyanobacteria algae, mosses, liverworts, hornworts and other bryophytes are growing or are expected to grow. Preferred species of mosses include *Antitrichia californica, Bryum argenteum, Barbula vinealis, Dendroalsia abietina, Dicranoweisia cirrrhata, Didymodon, Homalothecium fulgescens, Hoalothecium nutallii, Metaneckera menziesii, Neckerca douglasii, Peterogonium graile, Scleropodium cespitans, Tortula laevipila* var. *laevipila, Tortula laevipila* var. *meridionalis, Tortula latifolia, Tortula ruralis* and *Zygodon viridissimus*. Most preferred mosses include *Bryum argenteum*. Preferred species of liverworts include *Marcheantia, Conocephalum, Proella roellii* and *Porella navicularis*.

As set forth above, PPO-inhibiting herbicides, their agriculturally-acceptable salts, esters, acids, and metabolites find utility in controlling unwanted cyanobacteria algae, mosses, liverworts, hornworts and other bryophytes when applied by the methods of the present invention to a locus where the unwanted cyanobacteria algae, mosses, liverworts, hornworts and other bryophytes are growing. Examples of such PPO-inhibiting herbicides include, without limitation, one or more of acifluorfen-sodium, aclonifen, bifenox, chlomethoxyfen, chlornitrofen, ethoxyfen-ethyl, fluorodifen, fluoroglycofen-ethyl, fluoronitrofen, fomesafen, furyloxyfen, halosafen, lactofen, nitrofen, nitrofluorfen, oxyfluorofen, cinidon-ethyl, flumiclorac-pentyl, flumioxazin, profluazol, pyrazogyl, oxadiargyl, oxadiazon, pentoxazone, fluazolate, pyraflufenethyl, benzfendizone, butafenacil, fluthiacet-methyl, thidiazimin, azafenidin, carfentrazone ethyl, sulfentrazone, flufenpyr-ethyl, as well as other PPO-inhibiting herbicides, and their agriculturally-acceptable salts, esters, acids, and metabolites. A preferred PPO-inhibiting herbicide for control of unwanted cyanobacteria algae, mosses, liverworts, hornworts and other bryophytes is carfentrazone ethyl or one of the metabolites of carfentrazone ethyl, namely, i) α,2-dichloro-5-[4-(difluoromethyl)-4,5-dihydro-3-methyl-5-oxo-1H-1,2,4-triazol-1-yl]-4-fluorobenzenepropanoic acid (chloropropanoic acid), ii) 2-dichloro-5-[4-(difluoromethyl)-4,5-dihydro-3-methyl-5-oxo-1H-1,2,4-triazol-1-yl]-4-fluorobenzenepropenoic acid (cinnamic acid), iii) 2-dichloro-5-[4-(difluoromethyl)-4,5-dihydro-3-methyl-5-oxo-1H-1,2,4-triazol-1-yl]-4-fluorobenzoic acid (benzoic acid), and iv) 2-chloro-5-[4-(difluoromethyl)-4,5-dihydro-3-methyl-5-oxo-1H-1,2,4-triazol-1-yl]-4-fluorobenzenepropanoic acid (propanoic acid). A more preferred PPO-inhibiting herbicide for control of unwanted cyanobacteria algae, mosses, liverworts, hornworts and other bryophytes is carfentrazone ethyl.

Other analogs, homologs or derivatives of carfentrazone ethyl that find utility in the methods of the present invention include the following:

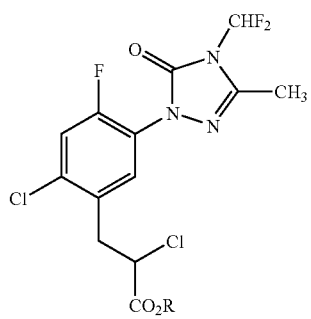

where R is selected from $CH_3$, $CH_2CH_2CH_3$, $CH(CH_3)_2$, $(CH_2)_3CH_3$, $CH_2CH(CH_3)_2$, n-pentyl, n-hexyl, $Na^+$, $K^+$, $Li^+$, $Ca^+$, and $NH_4^+$.

Carfentrazone ethyl, the metabolites, the analogs, homologs or derivatives set forth herein may be prepared by the methods taught in U.S. Pat. No. 5,125,958 or by methods analogous thereto, or by methods known to one skilled in the art.

Carfentrazone ethyl can be in a 1.9 EW formulation and used at a rate of from, about 3.4 fluid ounces per acre to about 13.4 fluid ounces per acre. Preferably, carfentrazone ethyl can be in a 1.9 EW formulation and used at a rate of about 6.7 fluid ounces per acre.

Locus or loci can include in, on or adjacent to lawns, gardens, trees, shrubs, golf courses, rooftops, decks and concrete structures.

Under certain conditions it may be advantageous in the control of unwanted cyanobacteria algae, mosses, liverworts, hornworts and other bryophytes to combine an effective amount of one or more of the PPO-inhibiting herbicides of the present invention with a second herbicide. Of particular advantage is the combination of one or more other herbicides that are known to have herbicidal activity on unwanted cyanobacteria algae, mosses, liverworts, hornworts and other bryophytes or are known for other uses, such as amines, esters, and salts of 2,4-D, dichloprop, dicamba, mecoprop, 2-methyl-4-chlorophenoxyacetic acid and various combinations of these products and atrazine, clopyralid, foransulfuron, glufosinate, glyphosate, halosulfuron-methyl, imazaquin, metsulfuron, quinclorac and triclopyr. A preferable combination of a PPO-inhibiting herbicide and a herbicide known for activity on unwanted cyanobacteria algae, mosses, liverworts, hornworts and other bryophytes is carfentrazone ethyl and one or more of amines, esters, and salts of 2,4-D, dichloprop, dicamba, mecoprop, 2-methyl-4-chlorophenoxyacetic acid and various combinations of these products and atrazine, clopyralid, foransulfuron, glufosinate, glyphosate, halosulfuron-methyl, imazaquin, metsulfuron, quinclorac and triclopyr.

Another embodiment of the present invention is the control of unwanted cyanobacteria algae, mosses, liverworts, hornworts and other bryophytes by a combination of an effective amount of one or more of the PPO-inhibiting herbicides of the present invention with one or more dispersing agents. Preferably, the dispersing agent is X-77 Spreader and is present in a concentration of about 0.25% volume/volume.

Yet another embodiment of the present invention is a composition suitable for controlling unwanted cyanobacteria algae, mosses, liverworts, hornworts and other bryophytes comprising an effective amount of a protoporphyrinogen oxidase enzyme-inhibiting herbicide, their agriculturally-acceptable salts, esters, acids, and metabolites.

As used in this specification and unless otherwise indicated the terms "protoporphyrinogen oxidase enzyme-inhibiting", "protoporphyrinogen oxidase enzyme-inhibitor", "PPO-inhibiting", or "PPO-inhibitor" as these terms relate to the herbicides used in the present invention are one and the same. The term "controlling" refers to the killing of, or minimizing the amount of cyanobacteria algae, mosses, liverworts, hornworts and other bryophytes to a point where they no longer impede the use of the areas described above.

The modifier "about" is used herein to indicate that certain preferred ranges are not fixedly determined. The meaning will often be apparent to one of ordinary skill. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

One skilled in the art will, of course, recognize that the formulation and mode of application of a toxicant may affect the activity of the material in a given application. Thus, for use in the control of unwanted cyanobacteria algae, mosses, liverworts, hornworts and other bryophytes, the PPO-inhibiting herbicides finding utility in the present invention may be formulated as granules of relatively large particle size, as water-soluble or water-dispersible granules, as powdery dusts, as wettable powders, as emulsifiable concentrates, as solutions, or as any of several other known types of formulations, depending on the desired mode of application. It is to be understood that the amounts specified in this specification are intended to be approximate only, as if the word "about" were placed in front of the amounts specified.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient in the total formulation.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders are in the form of finely divided particles, which disperse readily in water or other dispersant. The wettable powder is ultimately applied either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the herbicidal compound, 17.9 parts of Palmetto clay, and 1.0 part of sodium lignosulfonate and 0.3 part of sulfonated aliphatic polyester as wetting agents.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isphorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in certain formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long chain mercaptans and ethylene oxide. Many other types of useful surface—active agents are available in commerce. Surface-active agents, when used, normally comprise 1 to 15% by weight of the composition.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of a cover canopy. Pressurized sprays, typically aerosols wherein the active ingredient is dispersed in finely divided form as a result of vaporization of a low-boiling dispersant solvent carrier may also be used. Water-soluble or water-dispersible granules are free-flowing, non-dusty, and readily water-soluble or water-miscible. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The following examples further illustrate the present invention, but, of course, should not be construed as in any way limiting its scope. The examples are organized to present protocols for the evaluation of certain PPO-inhibiting herbicides when placed in contact with unwanted cyanobacteria algae, mosses, liverworts, hornworts and other bryophytes, and set forth certain biological data indicating the efficacy of such compounds.

Example 1

Efficacy Test of Carfentrazone Ethyl on Silver Moss (*Bryum argeliteum*)

Trials were conducted by spraying 0.67-13.4 fl oz/a of carfentrazone formulated as a 1.9 EW (Quicksilver T&O) onto bentgrass greens that were invaded by silver moss. Carfentrazone formulated as a 1.9 EW was also combined with X-77 Spreader (liquid at 0.25 wt % v/v basis) and sprayed at 6.7 fl oz/a. The bentgrass green was evaluated periodically after application. Percent (%) control or efficacy was determined as a percentage by volume reduction of the moss after spraying compared to an untreated reference. Four trials were conducted.

The results, shown as an average of the four trials, are compared with results observed in the same trials with Daconil at 174.2 fl oz/a application and a control of no application. The results and comparison are in Table 1 below.

TABLE 1

| % Efficacy/Control of Silver Moss in Bentgrass Greens | | | | | |
|---|---|---|---|---|---|
| | Rate fl oz/a | 6 Days | 13 Days | 21 Days | 30 Days | 44 Days |
| Quicksilver T&O | 0.67 | 85 | 45 | 30 | 33 | 15 |
| Quicksilver T&O | 3.4 | 85 | 64 | 71 | 54 | 38 |
| Quicksilver T&O | 6.7 | 85 | 58 | 48 | 66 | 37 |
| Quicksilver T&O | 13.4 | 55 | 28 | 41 | 26 | 33 |
| Quicksilver T&O + X-77 Spreader | 6.7 0.25% v/v | 89 | 71 | 70 | 81 | 72 |
| Daconil WS | 174.2 | 80 | 23 | 65 | 53 | 38 |
| Untreated | | 0 | 0 | 0 | 0 | 0 |

Example 2

Efficacy Test of Carfentrazone Ethyl on Silver Moss (*Bryum argenteum*) with Second Application Trials were conducted by spraying 0.67-13.4 fl oz/a of carfentrazone formulated as a 1.9 EW (Quicksilver T&O) onto bentgrass greens that were invaded by silver moss. Carfentrazone formulated as a 1.9 EW was also combined with X-77 Spreader (liquid at 0.25 wt % v/v basis) and sprayed at 6.7 fl oz/a. A second application was applied after 13 days. The bentgrass green was evaluated periodically after the second application. Percent (%) control or efficacy was determined as a percentage by volume reduction of the moss after spraying compared to an untreated reference. Four trials were conducted.

The results, shown as an average of the four trials, are compared with results observed in the same trials with Daconil at 174.2 fl oz/a application and a control of no application. The results and comparison are in Table 2 below.

TABLE 2

% Efficacy/Control of Silver Moss in Bentgrass Greens after Second Application

|  | Rate fl oz/a | 8 Days | 17 Days | 30 Days |
|---|---|---|---|---|
| Quicksilver T&O | 0.67 | 66 | 72 | 54 |
| Quicksilver T&O | 3.4 | 88 | 95 | 77 |
| Quicksilver T&O | 6.7 | 90 | 95 | 76 |
| Quicksilver T&O | 13.4 | 90 | 92 | 79 |
| Quicksilver T&O + X-77 Spreader | 6.7 0.25% v/v | 95 | 99 | 95 |
| Daconil WeatherStik | 174.2 | 86 | 90 | 87 |
| Untreated |  | 0 | 0 | 0 |

Example 3

Efficacy Test of Carfentrazone Ethyl on Silver Moss (*Bryum argenteum*)

Trials were conducted by spraying 24.4-73.2 mls per 1000 ft$^2$ of carfentrazone formulated as a 1.9 EW (Quicksilver T&O) onto bentgrass turf that was invaded by silver moss. Carfentrazone formulated as a 1.9 EW was also combined with X-77 Spreader (liquid at 0.25 wt % v/v basis) and sprayed at 24.4-36.6 mls per 1000 ft$^2$. The bentgrass turf was evaluated periodically after application. Control or efficacy was determined on a scale of 1-10 with 1 being the untreated control. Four trials were conducted.

The results, shown as an average of the four trials, are compared with results observed in the same trials with Terracyte at 8-16 lbs per 1000 ft$^2$ application, copper sulfate at 1.19 lbs per 1000 ft$^2$ and a control of no application. The results and comparison are in Table 3 below.

TABLE 3

Efficacy/Control of Silver Moss in Bentgrass Turf

|  | Rate per 1000 ft$^2$ | 2 Days | 14 Days | 28 Days | 50 Days |
|---|---|---|---|---|---|
| Quicksilver T&O | 24.4 ml | 2.7 | 4 | 6.7 | 8.3 |
| Quicksilver T&O + X-77 Spreader | 24.4 ml 0.25% v/v | 3 | 4.3 | 7 | 8.2 |
| Quicksilver T&O | 36.6 ml | 3.7 | 5 | 7.3 | 8.5 |
| Quicksilver T&O + X-77 Spreader | 36.6 ml 0.25% v/v | 3.3 | 5 | 7.7 | 8.7 |
| Quicksilver T&O | 73.2 ml | 4 | 5 | 7.8 | 8.7 |
| Terracyte | 8 lbs | 2 | 1.7 | 3.7 | 1.7 |
| Terracyte | 16 lbs | 2.3 | 3 | 4 | 4.7 |
| Copper Sulfate | 1.19 lbs | 1.7 | 2.7 | 3.3 | 6.3 |
| Untreated |  | 1 | 1 | 1 | 1 |

Example 4

Efficacy Test of Carfentrazone Ethyl on Cyanobacteria Blue-Green Algae

Trials were conducted by spraying 0.01-0.20 LB A/A of carfentrazone formulated as a 1.9 EW (Quicksilver T&O) onto Bermudagrass turf that was invaded by Cyanobacteria blue-green algae. Carfentrazone formulated as a 1.9 EW was also combined with Kinetic (liquid at 0.25 wt % v/v basis) and sprayed at 0.10 LB A/A. The Bermudagrass turf was evaluated periodically after application. Control or efficacy was determined by rating 'pest severity' on a scale of 1-9 with 1 being effective elimination of the algae. Three trials were conducted.

The results, shown as an average of the three trials, are compared with results observed in the same trials with Manzate 80 WP at 6.0 oz per 1000 ft$^2$ application and a control of no application or untreated. The results and comparison are in Table 4 below.

TABLE 4

Pest Severity of Cyanobacteria Blue-Green Algae in Bermudagrass Turf

|  | Rate LB A/A | Pre-Treatment | 1 Days | 3 Days | 7 Days | 14 Days | 21 Days |
|---|---|---|---|---|---|---|---|
| Quicksilver T&O | 0.01 | 4.63 | 4.20 | 4.97 | 5.50 | 5.97 | 6.00 |
| Quicksilver T&O | 0.05 | 5.20 | 4.97 | 2.40 | 2.07 | 3.50 | 3.93 |
| Quicksilver T&O | 0.10 | 5.30 | 4.77 | 1.33 | 1.20 | 1.20 | 1.67 |
| Quicksilver T&O | 0.20 | 5.20 | 4.87 | 1.00 | 1.00 | 1.00 | 1.00 |
| Quicksilver T&O + Kinetic | 0.10 0.25% v/v | 5.53 | 4.87 | 1.00 | 1.00 | 1.00 | 1.00 |
| Manzate 80 WP | 6.0 oz/ 1000 ft$^2$ | 5.20 | 5.00 | 1.33 | 1.87 | 2.93 | 4.20 |
| Untreated |  | 5.87 | 5.20 | 5.97 | 6.40 | 8.17 | 8.20 |

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for controlling unwanted *Bryum agrenteum* on golf course grass comprising applying an effective amount of protoporphyrinogen oxidase enzyme-inhibiting herbicides selected from the group consisting of carfentrazone ethyl and metabolites of carfentrazone ethyl to the golf course grass.

2. The method of claim 1, wherein said metabolites of carfentrazone ethyl are selected from i) α,2-dichloro-5-[4-(difluoromethyl)-4,5-dihydro-3-methyl-5-oxo-1H-1,2,4-triazol-1-yl]-4-fluorobenzenepropanoic acid, ii) 2-dichloro-5-[4-(difluoromethyl)-4,5-dihydro-3-methyl-5-oxo-1H-1,2,4-triazol-1-yl]-4-fluorobenzenepropenoic acid, 2-dichloro-5-[4-(difluoromethyl)-4,5-dihydro-3-methyl-5-oxo-1H-1,2,4-triazol-1-yl]-4-fluorobenzoic acid, and iv) 2-chloro-5-[4-(difluoromethyl)-4,5-dihydro-3-methyl-5-oxo-1H-1,2,4-triazol-1-yl]-4-fluorobenzenepropanoic acid.

3. The method of claim 1, wherein said carfentrazone ethyl is in a 1.9 EW formulation and used at a rate of from about 3.4 fluid ounces per acre to about 13.4 fluid ounces per acre.

4. The method of claim 3, wherein said rate is about 6.7 fluid ounces per acre.

5. The method of claim 1, wherein said protoporphyrinogen oxidase enzyme-inhibiting herbicide is combined with a second herbicide.

6. The method of claim 5, wherein said second herbicide is selected from the group consisting of amines, esters, and salts of 2,4-D, dichloprop, dicamba, mecoprop, 2-methyl-4-chlorophenoxyacetic acid and various combinations of these products and atrazine, clopyralid, foransulfuron, glufosinate, glyphosate, halosulfuron-methyl, imazaquin, metsulfuron, quinclorac and triclopyr.

7. The method of claim 1, wherein said protoporphyrinogen oxidase enzyme-inhibiting herbicide is combined with a dispersing agent.

8. The method of claim 7, wherein said dispersing agent is X-77 Spreader present in a concentration of about 0.25% volume/volume.

* * * * *